United States Patent
Reymond et al.

(10) Patent No.: US 7,238,483 B2
(45) Date of Patent: Jul. 3, 2007

(54) METHOD FOR DETECTING CATALYTIC ACTIVITY

(75) Inventors: Jean-Louis Reymond, Bulle (CH); Denis Wahler, Caissargues (FR)

(73) Assignees: Proteus SA (FR); Universite de Berne (CH)

(*) Notice: Subject to any disclaimer, the term of this patent is extended or adjusted under 35 U.S.C. 154(b) by 362 days.

(21) Appl. No.: 10/855,952

(22) Filed: May 28, 2004

(65) Prior Publication Data

US 2005/0014212 A1 Jan. 20, 2005

Related U.S. Application Data

(63) Continuation of application No. PCT/FR02/04097, filed on Nov. 28, 2002.

(30) Foreign Application Priority Data

Nov. 28, 2001 (FR) .................................. 01 15389

(51) Int. Cl.
| | |
|---|---|
| C12Q 1/48 | (2006.01) |
| C12Q 1/52 | (2006.01) |
| C12Q 1/68 | (2006.01) |
| C12N 1/42 | (2006.01) |
| G01N 33/53 | (2006.01) |

(52) U.S. Cl. .......................... 435/6; 435/7.2; 435/7.21; 435/7.4; 435/15; 435/16; 435/17; 435/18; 435/19; 435/20; 435/21; 435/22; 435/23; 435/24; 435/25; 435/26; 435/27; 435/28

(58) Field of Classification Search .................. 435/6, 435/7.4, 15, 16, 17–28, 7.2, 7.21
See application file for complete search history.

(56) References Cited

U.S. PATENT DOCUMENTS

| | | | | |
|---|---|---|---|---|
| 4,277,561 | A | * | 7/1981 | Monget et al. ................ 435/14 |
| 4,603,108 | A | | 7/1986 | Bascomb |
| 4,778,757 | A | * | 10/1988 | Teshima et al. .............. 435/28 |
| 5,122,602 | A | * | 6/1992 | Corey et al. ................ 536/17.2 |
| 5,162,203 | A | | 11/1992 | Vallee |
| 5,196,312 | A | * | 3/1993 | Miike et al. ................... 435/13 |
| 5,583,217 | A | | 12/1996 | Quante et al. |
| 5,846,754 | A | * | 12/1998 | Pugia et al. ................... 435/23 |
| 6,455,268 | B1 | * | 9/2002 | Jarnigan et al. .............. 435/18 |

FOREIGN PATENT DOCUMENTS

| | | |
|---|---|---|
| EP | 0 317 243 | 5/1989 |
| EP | 0 451 775 A1 | 10/1991 |
| EP | 0 796 854 A1 | 9/1997 |
| EP | 0 810 290 | 12/1997 |
| WO | WO 01 36662 | 5/2001 |
| WO | WO 01/36662 | 5/2001 |
| WO | WO 01/60986 | 8/2001 |
| WO | WO 01/61041 | 8/2001 |
| WO | WO 01/92563 A2 | 12/2001 |

OTHER PUBLICATIONS

Holzwarth et al., IR-thermographische erkennung katalytischer aktivitat in kombinatorischen bibliotheken heterogener katalysatoren, Angew. Chem. 1998, 110, Nr. 19, pp. 2788-2792.
Reetz et al., Eine methode zum high-throughput-screening von enantioselektiven katalysatoren, Angew. Chem. 1999, 111, Nr. 12, pp. 1872-1875.
Reetz et al., IR-Thermographie-Screening von thermoneutralen oder endothermen reaktionen: die ringschluss-Olefin-Metathese, Angew. Chem. 2000, 112, Nr. 7, pp. 1294-1298.
Reetz et al., IR-Thermographic screening of thermoneutral or endothermic transformations: The ring-closing olefin metathesis reaction, Angew. Chew. Int. Ed. 2000, 39, No. 7, pp. 1236-1239.
Badalassi et al., A versatile periodate-coupled flurogenic assay for hydrolytic enzymes, Angew. Chem. Int. Ed. 2000, 39, No. 22, pp. 4067-4070.
El-Kommos et al., Spectrophotometric Determination of some catecholamine drugs using metaperiodate, J. Assoc. Off. Anal. Chem. (vol. 73, No. 4, 1990), pp. 516-520.
Firestine et al., Using an araC-based three-hybrid system to detect biocatalysts in vivo, Nature Biotechnology, vol. 18, May 2000, pp. 544-547.
Klein et al., Enantioselective flurogenic assy of acetate hydrolysis for detecting lipase catalytic antibodies, Helvetica Chimica Acta, vol. 82 (1999), pp. 400-407.
Millar et al., Sex attractant pheromone of the pecan nut casebearer (lepidoptera: pyralidae), Bioorganic & Medicinal Chemistry, vol. 4, No. 3, pp. 331-339, 1996.
Moris-Varas et al., Visualization of enzyme-catalyzed reactions using pH indicators: rapid screening of hydrolase libraries and estimation of the enantioselectivity, Bioorganic & Medicinal Chemistry 7 (1999) pp. 2183-2188.
Suzuki, 4, 8 Dimethyldecanal: The aggregation pheromone of the flour beetles, Tribolium castaneum and T. confusum (Coleoptera: Tenebrionidae), Agric. Biol. Chem., 44, (10), pp. 25-19-2520, 1980.
Demirjian et al., Screening for novel enzymes, Top. Curr. Chem. (1999), vol. 200, pp. 1-25.
Jourdain et al., A stereoselective flurogenic assay for aldolases: Detection of an anti-selective aldolase catalytic antibody, Tetrahedron Letters 39 (1998), pp. 9415-9418.
Taran et al., Competitive immunoassay (Cat-EIA), a helpful technique for catalytic antibody detection, Part I, Tetrahedron Letters 40 (1999), pp. 1887-1890.
Matta et al., A rapid synthesis of $p$-nitrophenyl 2-$O$-$\alpha$-L-fucopyranosyl-$\beta$-D-galactopyranoside, Carbohydrate Research, 90 (1981), C1-C3.

Primary Examiner—Herbert J. Lilling
(74) Attorney, Agent, or Firm—Hunton & Williams LLP

(57) ABSTRACT

This invention has as its object a method for detecting catalytic activity of a sample, characterized in that it comprises: the incubation of a substrate (S) with the sample that may have the catalytic activity that it is desired to detect, the addition of a reagent (X) that can react either with a chemical group of unconsumed substrate (S) or with a chemical group of product (P) that is formed after an incubation period with the sample, the addition of a developer (R) that can react with reagent (X), and the detection of the transformation of developer (R).

20 Claims, 7 Drawing Sheets

OTHER PUBLICATIONS

N. Jourdian, R. Pérez Carlón, J.-L. Reymond, "A Stereoselective Fluorogenic Assay for Aldolase: Detection of an Anti-Selective Aldolase Catalytic Antibody", Tetrahedron Letters, NL, (1998), vol. 39, pp. 9415-9418.

G. Klein, J.-L. Reymond, An Enantioselective Fluorometric Assay for Alcohol Dehydrogenases Using Albumin-Catalyzed beta-Elimination of Umbelliferone, Bioorganic & Medicinal Chemistry Letters, (1998), vol. 8, pp. 1113-1116.

G-G. Chang, M-S Shiao, K-R Lee and J-J Wu, "Modification of human placental alkaline phosphatase by periodate—oxidized 1, N6 ethenoadenosine monophosphate", Biochem. J. (1990), pp. 683-690, vol. 273, Issue No. 3.

X-J. Chen, A. Archelas, R. Furstoss, Microbial Transformations. 27. The First Examples for Preparative-Scale Enantioselective or Diastereoselective Epoxide Hydrolyses Using Microorganisms. An Unequivocal Access to All Four Bisabolol Stereoisomers, J. Org. Chem. (1993), vol. 58, pp. 5528-5532, American Chemical Society.

Harris, Jennifer et al., "Rapid and general profiling of protease specificity by using combinatorial fluorogenic substrate libraries", PNAS (Jul. 5, 2000), pp. 7754-7759, vol. 97, No. 14.

M. T. Reetz, K.-E. Jaeger, "Superior Biocatalysts by Directed Evolution", Topics in Current Chemistry (1999), vol. 200, p. 31-57.

Geymayer, et al., "A General Fluorogenic Assay for Catalysis using Antibody Sensors", Chem. Eur. J., vol. 5, No. 3, p. 1006-1012, 1999.

Carlon, et al., "Fluorogenic Polypropionate fragments for detecting Stereoselective Algolases", Chem. Eur. J., vol. 6, No. 22, p. 4154-4162, 2000.

Gruninger-Leitch, et al., "Identification of beta-secretase-like activity using a mass spectrometry-based assay sysytem", Nature Biotechnology, vol. 18, p. 66-70, 2000.

Moris-Varas, et al., "Visualization of Enzume-Catalyzed Reactionsusing pH indicators: Rapid Screening of Hydrolase Libraries and Estimation of the Enantioselectivity", Bioorganic andMedicinal Chemistry, vol. 7, p. 2183-2188, 1999.

O'Brien, M. et al., "Enzymatic Profile of *Pseudomonas maltophilia*", Journal of Clinical Microbiology (Sep. 1982), pp. 417-421, vol. 16, No. 3.

Ronald G. Harvey, et al., "Synthesis of the Tumorigenic 3,4-Dihydrodiol Metabolites of Dibenz[a, j]lanthracene and 7,14-Dimet hydibenza[a, j]anthracene", J. Med. Chem., vol. 31, p. 1308-1312, 1988.

Nogare, et al., "Determination of Acetaldehyde and Acetone by the Iodoform Reaction", Anal. Chem., vol. 23, p. 1473-1478, 1951.

F. Badalassi, D. Wahler, G. Klein, P. Crotti, J-L Reymond, "A Versatile Periodate-Coupled Flourogenic Assay for Hydrolytic Enzymes", Angewandte Chemie. International Edition, Nov. 17, 2000, pp. 4067-4070, vol. 39, Issue No. 22.

D. C. Demirjian, P. C. Shah, F. Moris-Varas, "Screening for Novel Enzymes", Topics in Current Chemistry (1999), vol. 200, pp. 1-29.

S. Hanessian, T. Takamoto, R. Massé, G. Patil, "Aminoglycoside antibiotics: chemical conversion of neomycin B, paromycin, and lividomycin B into bioactive pseudosaccharides". Can. J. Chem. (1978), vol. 56, Issue No. 11, pp. 1482-1491.

M. T. Reetz, G. Lohmer, R. Schwickardi, "A New Catalyst System for the Heck Reaction of Unreactive Aryl Halides", Angewandte Chemie. International Edition (1998), vol. 37, Issue No. 4, pp. 481-483.

C. A. Roeschlaub, N. L. Maidwell, M. R. Rezai, P. G. Sammes, "A fluorescent probe for the detection of NAD(P)H", Chemical Communications (1999), pp. 1637-1638.

T. Suzuki, "4,8-Dimethyldecanal: The Aggregation Pheromone of the Flour Beetles, Tribolim castaneum and T.confusum (Coleoptera: Tenebrionidae)", Agric. Biol. Chem., (1980), vol. 44, pp. 2519-2520.

C. A. G. M. Weijers, A. L. Botes, M. S. Van Dyk, J. A. M. De Bont, "Enantioselective hydroysis of unbranched aliphatic 1,2-epoxides by Rhodatorula glutinis", Tetrahedron Asymmetry (1998), vol. 9, pp. 467-473.

J.G. Millar, A.E. Knudson, S. McElfresh, R.Gries, G. Gries, J.H. Davis). Bioorganic & Medicinal Chemistry, (1996), vol. 4, Issue No. 3, pp. 331-339.

G. Klein, J.-L. Reymond, "Enantioselection Fluorogenic Assay of Acetate Hydrolysis for Detecting Lipase Catalytic Antibodies", Helvetica Chimica Acta (1999), vol. 82, pp. 400-407.

J. Latip, T. G. Hartley, P. G. Waterman, "Lignans an coumarins metabolites from *Melicope hayesii*", Phytochemistry, May 1999, vol. 51, Issue No. 1, pp. 107-110.

B. List, C. F. Barbas, R. A. Lerner, "Aldol sensors for the rapid generation of tunable fluorescence by antibody catalysis", Proceedings of the National Academy of Sciences, USA, Dec. 22, 1998, vol. 95, Issue No. 26, pp. 15351-15355.

T. Matsumoto, Y. Takeda, E. Iwata, M. Sakamoto, T. Ishida, "Lipase-Catalyzed Hydrolysis of Some Racemic 1-Acetoxy-2-arylpropanes", Chemical & Pharmaceutical Bulletin, (1994), vol. 42, Issue No. 6, pp. 1191-1197.

K. L. Matta, C. F. Piskorz, J. J. Barlow, "A rapid synthesis of p-nitrophenyl 2-O-ÿ-L-fucopyranosyl-ÿ-D-galctopyranoside", Carbohydrate. Research, (1981), vol. 90, pp. C1-C3.

* cited by examiner

Sample

Noradrenaline    Catechols

Octopamine    Aesculetin   2,3-Dihydroxynaphthalene

Vegetable oils (2a-c)     4     Phytic acid (5)

Tributyrin (3, R = $C_3H_7$)

METHOD FOR DETECTING CATALYTIC ACTIVITY

CROSS-RELATED AND PRIORITY APPLICATIONS

The present application is a continuation of International Application No. PCT/FR02/04097, filed Nov. 28, 2002, which claims the benefit of French Patent Application No. 01/15389, filed Nov. 28, 2001. The disclosures of these priority applications are hereby incorporated by reference in their entirety.

FIELD OF INVENTION

This invention relates to a method for detecting catalytic activity of a sample.

BACKGROUND OF INVENTION

To develop new biocatalysis processes that are useful in particular to the chemical and pharmaceutical industry and to the engineering of proteins, it is necessary to use methods for detecting reliable, fast, and low-cost catalytic activities.

In the prior art, there are two types of substrates that allow the detection of catalytic activity.

On the one hand, substrates of the type modified by a detectable group that can release a signal after their transformation by a particular catalytic activity, and, on the other hand, the techniques that use natural-type substrates as indicated below are known.

Among the modified substrates, it is possible to use substrates such as aromatic alcohol ester that release, after their transformation, a tinted or fluorescent aromatic alcohol (D. C. Demirjian et al. Top. Curr. Chem. 1999, 200, 1). These substrate types have a major disadvantage, because the chromogenic molecule or fluorogenic molecule is a highly activated group, which makes these substrates unstable. The detection reactions that are derived therefrom consequently can be non-specific.

A second class of modified substrates results in the revelation of a product that is obtained after secondary enzymatic reaction and/or spontaneous reaction (N. Jourdain et al. Tetrahedron Lett. 1998, 39, 9415; K. L. Matta et al., Carbohydr. Res. 1981, 90, C1–C3; G. Klein and J. L. Reymond, Helv. Chim. Acta 1999, 82, 400). This second class of substrates is more stable. This second class of substrates, however, is limited to particular uses. Actually, the dosage of the reaction is done directly on the released product by using an enzyme. The released product should therefore correspond to very specific structural characteristics, which thereby limits the diversity of catalytic activities that can be detected.

A third class of modified substrates has been developed to detect catalytic activities by avoiding the problems raised in advance (Badalassi, F. et al. Angew Chem Int Ed Engl. 2000, 39 (22): 4067–4070). These substrates, however, always correspond to modified substrates.

In contrast, the natural substrates that can demonstrate a catalytic activity are known. The various techniques, however, that use natural substrates are often complex and cumbersome to use for high-flow screening (cumbersome instrumentation in the case of the IR thermography, CE, HPLC, GC MS) or limited to particular catalytic activities that can, for example, induce a difference in pH and/or in the narrowly defined reaction conditions (measurement of pH variations, secondary enzymes). Most of these measurements are also very expensive to carry out because of the cost or the instrumentation, or reagents involved, in particular the secondary enzymes and the anti-product antibodies (M. T. Reetz et al Angew. Chem. 1999, 1111, 1872; A. Holzwarth et al. Angew. Chem. 1998, 110, 2788; M. T. Reetz et al. Angew. Chem. 2000, 112, 1294, Angew. Chem. Int. Ed. Engl. 2000, 39, 1236; Taran et al. Tetrahedron Lett. 1999, 40, 1887, 1891, S. M. Firestine et al. Nat. Biotechnol 2000, 18, 544; F. Moris-Varas et al. Bioorg. Med. Chem. 1999, 7, 2183).

SUMMARY OF INVENTION

This invention aims at offering a method for detecting catalytic activity that is free of the various technical problems cited above and that makes possible the use of all types of substrates.

This object is reached thanks to a method for detecting catalytic activity of a sample that comprises:
  Bringing a substrate (S) into contact with the sample that may have the catalytic activity that it is desired to detect,
  The addition of a reagent (X) that can react either with a chemical group of substrate (S) or with a chemical group of product (P) that is formed,
  The addition of a developer (R) that can react with reagent (X),
  The detection of the transformation of developer (R).

Reagent (X) is added after an incubation period between substrate (S) and the sample. Reagent (X) reacts, after a given incubation period, with either substrate (S) that is not consumed by the catalytic activity of the sample or product (P) that is formed. The catalytic activity thus can be measured over time.

DETAILED DESCRIPTION OF PREFERRED EMBODIMENTS

It is possible to differentiate two embodiments of the method of the invention:
  A first embodiment where reagent (X) is modified by substrate (S) and not by product (P),
  A second embodiment where reagent (X) is modified by product (P) and not by substrate (S).

The diagrams of FIGS. 1 and 2 illustrate the method of the invention according to which respectively (S) or (P) is capable of reacting with reagent (X).

The method of the invention is based on the implementation of the trio: (S) or (P)/(X)/(R), where reagent (X) is able to react with (S) or (P) and developer (R).

The method of the invention is based on a cascade of reactions where the amount of equivalents of reagents (X) is less than the sum of the amount of equivalents of (S) that is not consumed or of (P) that is formed and equivalents of developers (R).

The amount of equivalents of developer (R) that is used is advantageously greater than or equal to the amount of equivalents of reagents (X).

By way of example, a detection of the catalytic activity can be carried out by using an amount of reagent (X) that corresponds to 1× the maximum amount of (P) that is expected or (S) that is transformed according to the case where reagent (X) reacts with either (P) that is formed or (S) that is not consumed.

The catalytic activity of the sample that is detected according to the method of the invention can be chemical or enzymatic. It corresponds to any activity that can transform a substrate (S) into a product (P). The transformation of (S) into (P) can be carried out by several sequential reactions.

The sample that can contain said catalytic activity can stem from various origins. It can be, for example, chemical, biological, microbiological, animal, vegetable, or human. It can stem from all types of environments and samplings. The sample can be simple or complex, prepared from standard extraction techniques, then optionally purified or used just as is.

The catalytic activity that is detected by the method of the invention can correspond to a new activity of a known catalyst. Advantageously, the catalytic activity corresponds to an enzyme. This activity can correspond to that of an enzyme or a mixture of enzymes.

This enzyme is selected from the group that comprises hydrolases, oxydases, lyases, ligases, transferases, and isomerases.

Substrate (S) can correspond to any molecule that can be used for detecting a catalytic activity according to the method of the invention. The substrate is therefore specific to the desired catalytic activity. It may correspond to all types of substrates like a natural or synthetic substrate that can be modified or not. The natural substrate can correspond by way of example to vegetable oils for detecting lipase-type catalytic activities.

Reagent (X) corresponds to any molecule that can react with a chemical group that is present either on substrate (S) or on product (P) but not with both.

Chemical group is defined as any group that is present on substrate (S) or product (P) and optionally on developer (R) that can react with reagent (X). They can correspond by way of example to 1,2-diol, 1,2-amino alcohol, 1,2-diamine, alpha-hydroxyketone, alpha-aminoketone, thiol, thioether, 1,2-catechol, or hydroquinone (=1,4-dihydroxybenzene) groups that can react with reagent (X) that can be an oxidizing agent like the periodate.

The selection of reagent (X) is made based on the catalytic activity that it is desired to detect. It is selected so as to be able to react, as seen above, with a chemical group, either (P) that is formed or (S) that is not consumed after an incubation period with the sample. It should not react simultaneously with (S) and (P).

In the case where reagent (X) reacts with product (P), it is possible to add reagent (X) during the catalytic transformation from S into P to the extent that reagent (X) does not affect the catalytic activity or the transformation of (S) into (P) and to the extent that reagent (X) withstands the conditions of transformation of S into P. By way of example, the incubation of the reagent corresponding to the periodate at a very high temperature will be avoided. In addition, if the reaction uses an intermediate product (P') that can react with reagent (X), but that can again be transformed into final product (P), it is also preferable not to add the reagent before the end of the transformation of (S) into (P).

Developer (R) is able to react with reagent (X). In addition, the transformation of developer (R) by said reagent (X) can be detected directly or indirectly. Finally, the detection of developer (R) is insensitive to (S) and (P).

The detection of the transformation of developer (R) by reagent (X) may correspond to the appearance of a signal or else to the extinction of a signal. According to the presence or the absence of this signal, it is possible to make a conclusion on the performance of the catalytic transformation of (S) into (P).

In a particular form, developer (R) can react with transformed reagent (X). In this case, however, the signal that is measured with transformed reagent (X) should be different from the one that is measured with reagent (X).

Developer (R) is selected so as to react with reagent (X) to provide a detectable compound. By way of example, reagent (X) can modify a chemical group of developer (R) to provide a detectable compound, or developer (R) can form with reagent (X) a detectable non-covalent complex that can in particular be chromogenic.

In the case where developer (R) has a chemical group that can react with reagent (X), the chemical group of developer (R) is transformed by reagent (X).

In the case where the developing uses a chemical group of developer (R), the chemical groups of (S) or (P) and of developer (R) that are able to react with reagent (X) can be different or identical.

Developer (R) can correspond to a molecule that can be the substrate of a catalytic reaction or a series of catalytic reactions that are different from those that are able to transform (S) into (P).

In a specific implementation of the invention, the following trio is used: (reagent (X)=chemical oxidizing agent/(S) or (P) and developer (R) that may have the following chemical groups: 1,2-diol or 1,2-amino alcohol or 1,2-diamine or alpha-hydroxyketone or alpha-aminoketone or thiol, thioether, or catechol, or catecholamine, or hydroquinone).

Substrate (S) is selected so as to react with the sample that can contain the catalytic activity that it is desired to detect. In this implementation, substrate (S) or product (P) corresponds to a compound of formula (I) below:

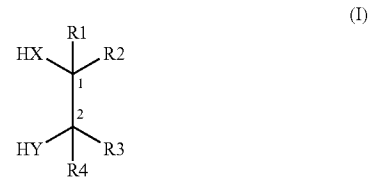

(I)

in which the C1-C2 bond is sensitive to a cleavage by a chemical oxidation reaction.

R1 to R4, identical or different, correspond to a hydrogen atom, an alkyl group that may or may not be substituted, or a functional group that may or may not be substituted.

X and Y, identical or different, are selected from among an oxygen atom, a sulfur atom, an amine of formula —NR8R9; R8 is selected from among: a hydrogen atom, an alkyl group, an aryl group, that may or may not be substituted, and R9 is not a hydrogen atom.

A functional group is defined as any chemical group that belongs to a class of organic compounds characterized by chemical properties. It is possible to cite by way of example of a functional group: amides, acyls, alkoxy, nitriles, aryls, heteroaryls, alkenyls, carbonyls, thiocarbonyls, carboxyls, thiocarboxyls, carbamyls, thiocarbamyls, thiocarbamides, alcohols, thiols, and amines that may or may not be substituted.

In a preferred form, product (P) corresponds to formula (I) above.

Reagent (X) is selected so as to be able to react with (S) or (P) of formula (I). In a particular implementation, reagent (X) corresponds to a chemical oxidizing agent that can cleave the C1-C2 bond of (S) or (P) of formula (I).

The chemical oxidizing agent can correspond in an advantageous and non-limiting manner to one or more of the following reagents: $H_5IO_6$, $RuO_2,OsO_4$, $(CH_3CH_2CH)_4N$ $(RuO_4)$, $NaClO_4$, $NaIO_4$, $Na_3H_2IO_6$, $NaMnO_4$, $K_2OsO_4$, $KIO_4$, $KMnO_4$, $KRuO_4$, $K_2RuO_4$, LiOCl, lead acetate, tetrapropyl ammonium periodate, chromic acid or salts of the latter, $NaBiO_3$, $Ph_3BiCO_3$, $Ca(OCl)_2$, reagents Ce(IV), Cr(VI), salts of Co(II), IOAc, I(OAc)$_3$, N-iodosuccinimide, VO(acac), Pb(OAc)$_4$, $MnO_2$, $H_2O_2$ or mixture of reagents [$H_2O_2$, $Na_2WO_4$, $H_3PO_4$].

Quite preferably, the oxidizing chemical agent is a periodate salt.

By way of example, it is possible to cite the three development forms that are described below.

In an implementation, developer (R) is selected from among the nitrophenol amino alcohol and the catechols of the following formulas:

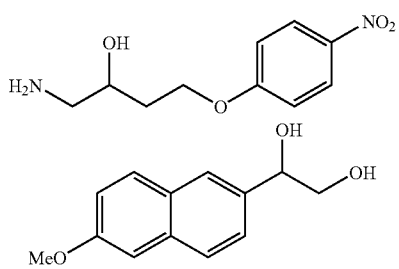

"nitrophenol amino alcohol" 6-methoxy-2-(1',2'-dihydroxy-4-(p-nitrophenoxy)-1-amino-ethyl) naphthalene-2-butanol Among developers (R) of the periodate that have not reacted with S or P, it is possible to cite in particular the nitrophenol amino alcohol and the catechols.

The (1,2-dihydroxybenzene) catechols generally provide reactions with the periodate that result in a change in optical density, and sometimes changes in fluorescence. The adrenaline and the noradrenaline are preferred developers of this implementation. They provide a red color in an extremely short time by reacting with the periodate. It is not obvious to one skilled in the art that the adrenaline can be used as a quantitative developer of the periodate. Actually, the quinones that are produced from the oxidation break down over time to form polymers. In addition, this development uses a double oxidation. The examples from the literature (El-Kommos el al (1990). J. Assoc. Off. Anal. Chem., 73, 516–520) do not teach the fact that the second oxidation is visibly faster than the first, which makes possible a conversion of the adrenaline into adrenochrome even with very little periodate relative to the adrenaline. Thus, it is not absolutely obvious to use the trio (reagent=periodate/S or P=compound of formula I/developer=catechol) to detect a catalytic activity according to the method of the invention.

This principle of catalytic activity development that uses the periodate as a reagent (X) and adrenaline as developer (R) is illustrated in FIG. 3.

The octopamine can also be used as a developer of the periodate, whose oxidation of the 1,2-amino alcohol group releases p-hydroxybenzaldehdye, which shows strong absorbance at 330 nm (close to UV, easily detectable).

FIG. 4 provides examples of catechol-type $NaIO_4$ developer (R).

In another implementation, developer (R) corresponds to a compound of formula (I) that can be detected after having reacted with reagent (X).

The developer that corresponds to a compound of formula (I), described above, exhibits the particular feature of being able to be detected after having reacted with reagent (X) that is not transformed by (S) that is not consumed or (P) that is formed after an incubation period with the sample.

According to a first implementation of direct development, developer (R) that corresponds to formula (I) is oxidized in the presence of reagent (X), according to the following reaction diagram:

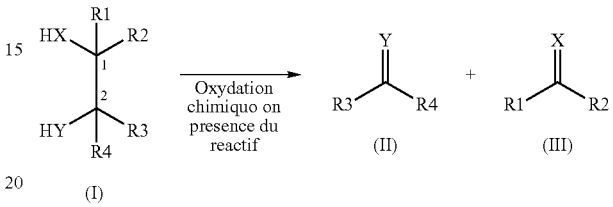

[Chemical oxidation in the presence of the reagent]

The properties of the products of formulas (II) and/or (III) that are released can then be detected directly.

By way of nonlimiting examples, it is possible to cite, among these properties of compounds of formulas (II) and/or (III), a physical property, such as solubility, a physico-chemical property, such as a spectral property, or a biological property, such as the activation, of an enzyme, an odor, or the action of a pheromone.

The compounds of formulas (II) or (III) may correspond to aromatic ketones, for example a beta-aromatic ketone that is detected by a spectral variation, an aldehyde such as benzaldehyde, or the citronellal that is detected by the odor or with a pheromone that is detected by the attraction of insects. (Suzuki et al., (1980), Agric. Biol. Chem. 44, 2519; Millar et al. (1996), Bioorg. Med. Chem. 3, 331–340).

In a second indirect development method, at least one of groups R1 to R4 of the compound of formula (I) corresponds to formula (IV) below:

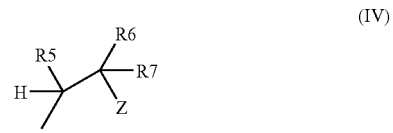

in which:

R5, R6 and R7, identical or different, represent a hydrogen atom, an alkyl group that may or may not be substituted, or a functional group that may or may not be substituted, and Z is a precursor of a detectable product ZH.

Developer (R) of formulas (I), in the presence of the reagent, is oxidized to release, by way of example, the compounds of formulas (V) and (III). The compound of formula (V) undergoes an advantageously spontaneous beta-elimination reaction that leads to the detectable ZH product, according to the following reaction diagram:

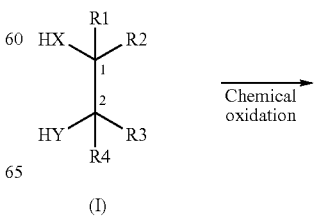

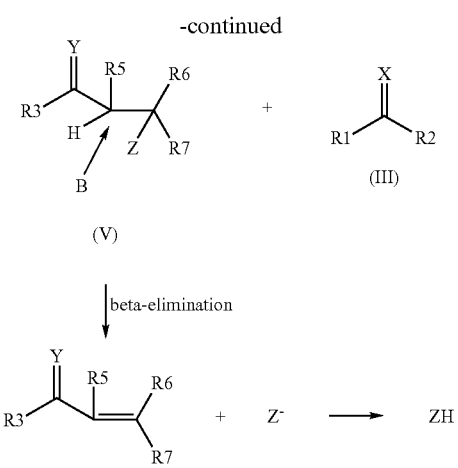

This advantageously spontaneous beta-elimination reaction is preferably carried out in the presence of a base that is referred to as "B" in the diagram above that may correspond to the bovine serum albumin (BSA).

Among the properties of the ZH compound, it is possible to cite, by way of nonlimiting examples, a physical property such as solubility, a physico-chemical property such as a spectral property or a biological property such as the induction of bacterial growth.

The ZH compound is selected from among an aromatic alcohol a heteroaromatic alcohol, a heteroaromatic amine, a halogen atom, or a phosphoric ester. By way of nonlimiting examples, the following can be cited: fluorescein, phenolphthalein, phenol red, p-nitrophenol, o-nitrophenol, 2,4-dinitrophenol, 6-hydroxynaphthoic acid, 8-hydroxy-pyrene 1,3,6-trisulfonic acid, tyrosine, luciferin, indolyl, 5-bromo-4-chloro-indolyl, quinolinium, nitro-anilinium, or pyridoxamine.

In a third development method, developer (R) corresponds to formula (I) in which:
  One of R1 to R2 and one of R3 to R4 has the same meaning as above,
  The others R1 or R2 and R3 or R4 interact with one another.

In this case, the cleavage of the C1-C2 bond from the developer of formula (I), brought into the presence of the reagent, produces a detectable spectral variation.

A non-limiting example of interaction between R1 or R2 and R3 or R4 is a FRET (Fluorescent Resonance Energy Transfer)-type energy transfer.

Finally, the developer can also correspond to the precursor of an inhibitor of a catalyst.

In the presence of reagent (X), the precursor of the inhibitor is transformed into an inhibitor of a catalyst of a detectable reaction. This catalyst is different from the catalytic activity that it is desired to detect with the process of the invention. The inhibitor may correspond by way of example to the phenol, and the corresponding precursor may correspond in particular to a compound of formula (V) below:

(VI)

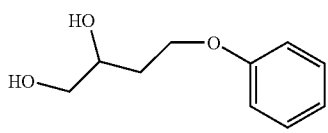

This trio (reagent (X)=chemical oxidizing agent/S or P and developer (R) whose chemical groups correspond to 1,2-diol or 1,2-amino alcohol or 1,2-diamine or alpha-hydroxyketone or alpha-arninoketone or thiol, thioether, catechol or catecholamine or hydroquinone) makes it possible by way of example to detect, according to the process of the invention, phytases, lipases, epoxide hydrolases, amidases, acylases or esterases.

In another implementation of the invention, the trio below is used: (reagent (X)=Dansylhydrazine/(S) or (P) and developer (R) whose chemical groups correspond to ketones or aldehydes or alcohol-type hemiacetals).

Substrate (S) is always able to react with the catalytic activity that it is desired to detect.

In another implementation, substrate (S) or product (P) corresponds to aldehydes or ketones O═C (molecule). The detection of catalytic transformation is therefore done in the following way by way of example. As reagent (X), a fluorescent hydrazine F—NHNH2 (F corresponding to a fluorophore), which forms the fluorescent product F—NH—N═C (molecule), is used. Then, the F—NHNH2 reagent, not having reacted with S or P, is dosed with a developer R) that corresponds to an aldehyde or a quenching ketone Q-C═O (Q corresponding to a quencher), which forms the non-fluorescent pair Q-CH═N—NH—F.

It is possible to design a method for detecting an equivalent catalytic activity that can transform a substrate (S) into a product (P) where (S) or (P) has the following chemical groups: aldehydes or ketones O═C (molecule) or hemiacetals of sugar type, and:

1) Reagent (X) is a quenching hydrazine (example: 4-carboxy-phenyl-hydrazine) of Q-NH—NH2 type, and developer (R) is a fluorescent aldehyde or ketone F—CHO (example: 6-methoxy naphthaldehyde). The reaction between reagent (X) that is not consumed by (S) or (P) and developer (R) corresponds to an extinction of fluorescence.

2) Reagent (X) is a fluorescent hydrazine F1-NHNH2, and developer (R) is an aldehyde or ketone F2-CHO. The reaction between reagent (X) that is not consumed by (S) or (P) and developer (R) corresponds to a FRET-type phenomenon between F1 and F2 that can be observed. By way of example, F1 =fluorescein thiosemicarbazide and F2 =rhodamnine aldehyde.

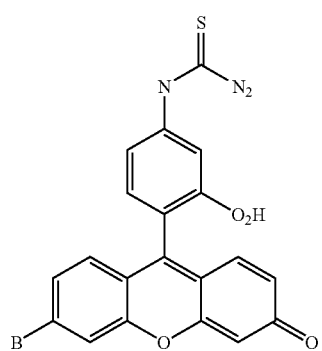

Fluorescein thiosemi-Carbazide

-continued

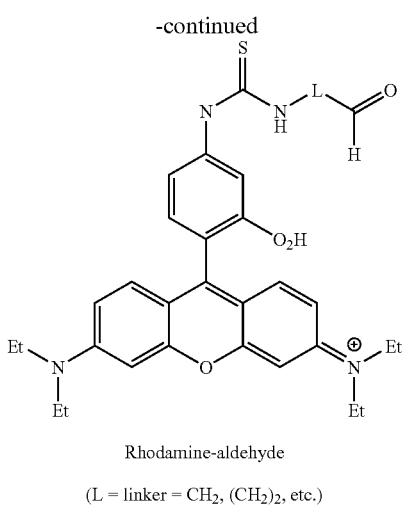

Rhodamine-aldehyde (L = linker = CH$_2$, (CH$_2$)$_2$, etc.)

This type of trio (reagent (X)=Dansylhydrazine/(S), or (P) and developer (R) whose chemical groups correspond to ketones or aldehydes or hemiacetals of sugar type) makes it possible by way of example to detect according to the process of the invention the oxidation or the reduction of ketones and aldehydes, the oxy-Cope reaction, the oxidative cleavage of double bonds and diols, the reductive dimerization of aldehyde or ketone, the reduction amination of aldehyde or ketone, the additions of various nucleophiles to the ketones and aldehydes (cyanide, bisulfite, etc.), and the reactions of aldolization and retro-aldolization.

Other trios can be considered for carrying out the method of the invention. It is also possible to cite the trios below:
  (S or P whose chemical groups correspond to aldehydes, ketones or hemiacetals of sugar type/X=NaCN, NaBH4, NaHSO3/R=6-methoxynaphthaldehyde) where developer (R) that has reacted with reagent (X) that is not consumed or is transformed by (S) or (P) becomes non-fluorescent.
  (S or P whose chemical group corresponds to RCOOH (carboxylic acid)/X=NaOH/R=4-nitrophenol) where developer (R) that has reacted with reagent (X) that is not consumed or transformed by (S) or (P) induces a change in pH.

The method of the invention exhibits great flexibility. It can be used on any type of substrate. Actually, it is possible in particular to measure the activity of lipases on oils at any pH between 2 and 10, with or without co-solvents, by colorimetry.

The method for detecting catalytic activities of this invention makes it possible to be completely independent of the structure of substrates; it is possible to use any type of specific substrates that are natural or modified by a given catalytic activity. By way of example, it is possible to cite the use of a precursor of diol or hydroxyketones, in particular natural substrates, as shown here with the use of a vegetable oil as a substrate or else the screening of the benzoin-type condensation that is catalyzed by the decarboxylase pyruvate, which provides a hydroxyketone starting from benzaldehyde and pyruvate.

The method of the invention makes it possible to measure catalytic activity over a great diversity of substrates. It is possible to cite, for example, the activity of epoxide hydrolases over a great diversity of substrates, which is not possible other than in a simple colorimetric manner. Actually, it would otherwise be necessary to determine the formation of each product separately by HPLC, GC or another cumbersome analytical method.

In addition, with the method of the invention, it is possible to follow reactions where the diol (amino alcohol or diamine) is used as a substrate and disappears during the reaction.

Within the context of high-flow detection, the method of the invention makes it possible to use commercial substrates, which makes it possible to quickly have an extended class of substrates. This is well illustrated in the examples below.

The method of the invention can also be used for detecting the transformation of a substrate (S) into a product (P) by a catalytic activity.

The invention therefore also relates to the use of a method for detecting a catalytic activity of a sample that is described above for the detection of a catalytic transformation of a substrate (S) into a product (P).

Finally, the invention has as its object a sample that exhibits a catalytic activity that can transform a substrate (S) into a product (P) that is demonstrated by the method described above.

Other advantages and characteristics of the invention will come out in the following examples where reference will be made to attached drawings in which:

EXAMPLES

Example 1

Detection of Lipase and Esterase Activities

Figure 1:
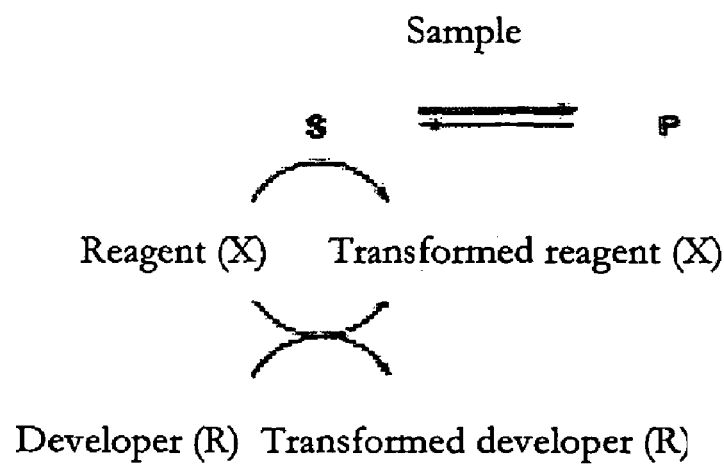
FIG. 1 is a diagram of the method of the invention where reagent (X) reacts with substrate (S).
Figure 2:
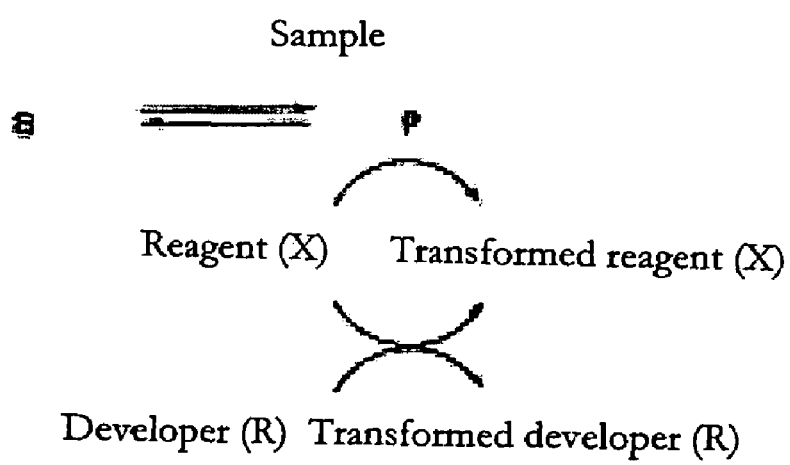
FIG. 2 is a diagram of the method of the invention where reagent (X) reacts with product (P).
Figure 3:
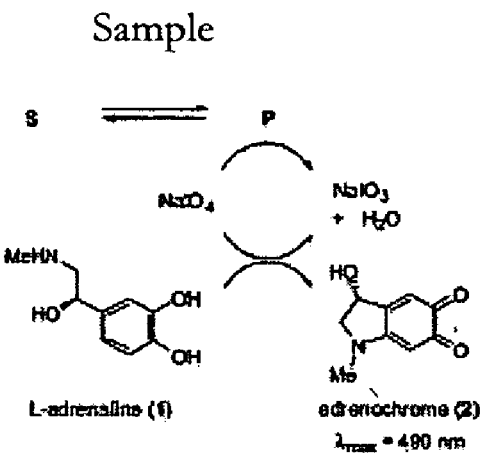
FIG. 3 illustrates the principle of the method of the invention using the periodate as reagent (X) and adrenaline as developer (R).
Figure 4:
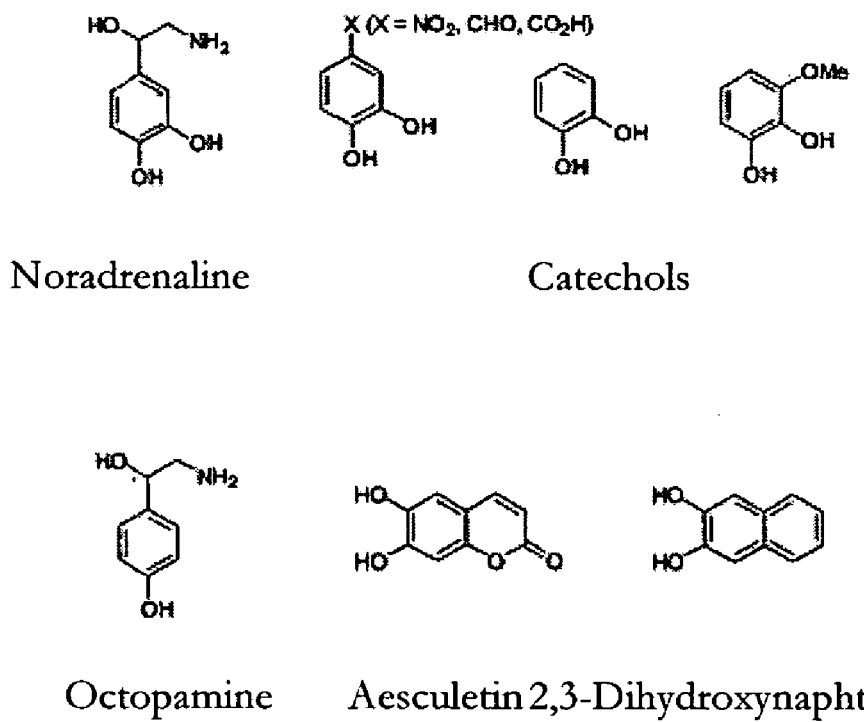
FIG. 4 represents examples of catechol-type NaIO$_4$ developer (R).
Figure 5:
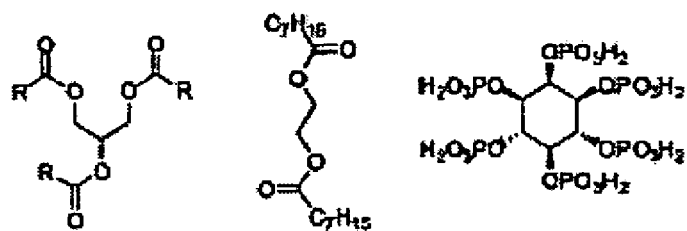
FIG. 5 shows the substrates of enzymes that are used in the following examples.
Figure 5:
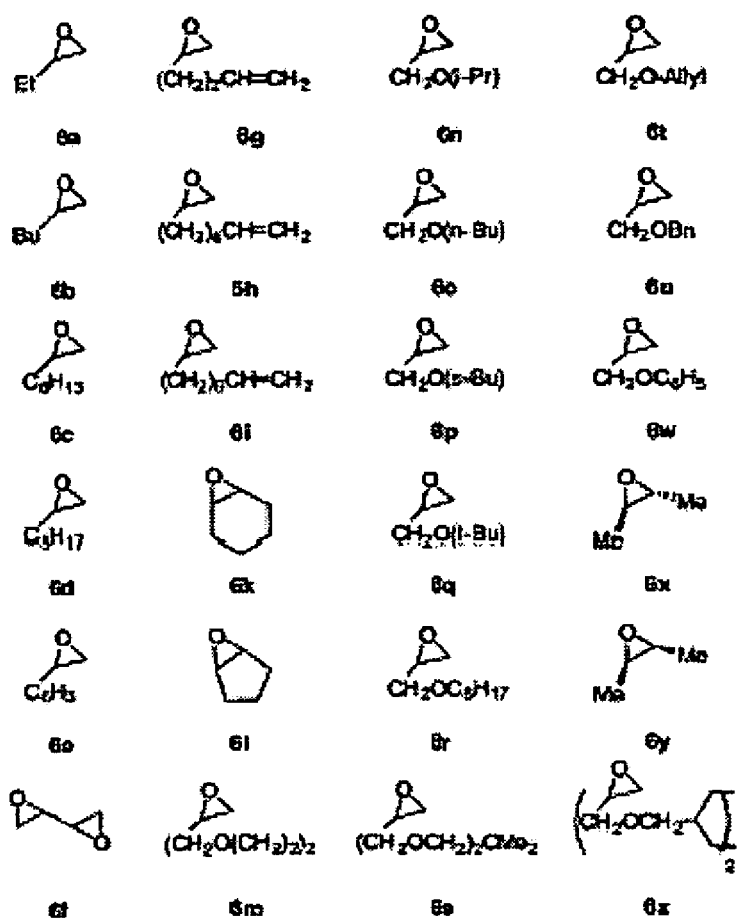

The detection reactions are carried out with 5 substrates that are described in FIG. 5. Three concentrations of enzymatic activities are tested for carrying out the detection.

1) First Implementation.
   i) The enzymes that are diluted in a phosphate buffer, 20 mmol, pH 7.2, are added to substrates that correspond to vegetable oils 2a–c (0.05 ml in 0.4 ml of buffer in a 1.5 ml Eppendorf tube with a 1200 rpm stirring mechanism) or substrates 3 or 4 (10 mmol) at 26° C. for 60 minutes. These different substrates are present in FIG. 5.
   ii) Addition to the level of the preceding catalytic reaction for 30 minutes of a reagent corresponding to 1 mmol of $NaIO_4$, capable of reacting chemically with product P.
   iii) Addition of 1.5 mmol of the developer $NH_2CH_2CHOHCH_2CH_2OC_6H_4NO_2$ (=nitrophenol amino alcohol)+2 mg.ml$^{-1}$ of BSA, 60 minutes.

Figure 6:
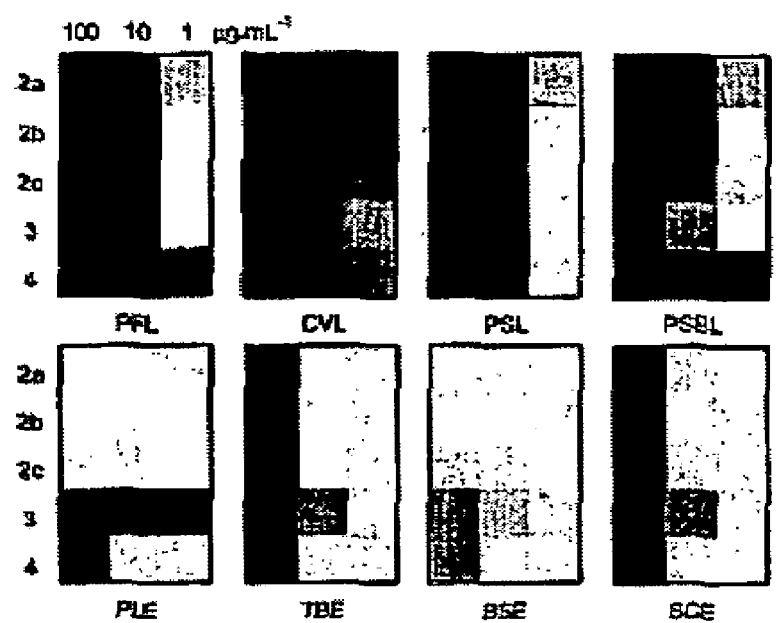
FIGS. 6 and 7 show the detection of lipase and esterase activities by the method of the invention respectively by using as developer the nitrophenolanino alcohol and adrenaline.

FIG. 6, attached, reports the results of detection of lipase and esterase activities with vegetable oils (2a=olive oil, 2b=sunflower seed oil, 2c=grapeseed oil), tributyrin (3) and ethylene glycol bis-octanoate (4). The tinted zones go from white (no activity, no reduction in color of the nitrophenol) to black (no color left from nitrophenol, maximum activity). Abbreviations of the tested samples (Fluka): PFL=*Pseudomonas fluorescens* lipase (F62321); CVL=*Chromobactenium viscosum* lipoprotein lipase (F62333); PSL=*Pseudomonas* sp. lipoprotein lipase (F62335); PSBL=*Pseudomonas* sp. Type B lipoprotein lipase (F62336); PLE=pig liver esterase (F46058); TBE=*Thermoanaembium brockii* esterase (F46061); BSE=*Bacillus* sp. esterase (F46062); SCE=*Saccharomyces cerevisiae* esterase (F46071).

2) Second Implementation.
   i) The enzymes that are diluted in a phosphate buffer, 20 mmol, pH 7.2, are added to substrates that correspond to vegetable oils 2a–c (0.05 ml in 0.4 ml of buffer in a 1.5 ml Eppendorf tube with a 1200 rpm stirring mechanism) or substrates 3 or 4 (10 mmol) at 26° C. for 30 minutes with 1 mmol of $NaIO_4$. These different substrates are present in FIG. 5.
   ii) Addition of 1.5 mmol of adrenaline, 5 minutes.

Figure 7:
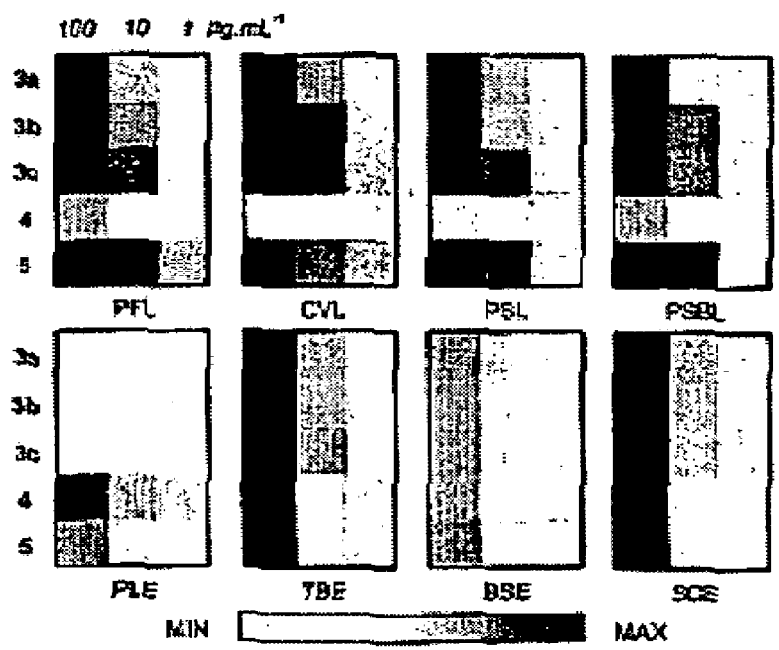

FIG. 7, attached, illustrates the results of detection of lipase and esterase activity with vegetable oils (2a=olive oil, 2b=sunflower seed oil, 2c=grapeseed oil), tributyrin (3) and ethylene glycol bis-octanoate (4). The tinted zones go from white (no activity, no reduction in color of the adrenochrome) to black (no color left from the adrenochrome, maximum activity). Abbreviations of the tested samples (Fluka): PFL=*Pseudomonas fluorescens* lipase (F62321); CVL=*Chromobacterium viscosum* lipoprotein lipase (F62333); PSL=*Pseudomonas* sp. lipoprotein lipase (F62335); PSBL=*Pseudomonas* sp. Type B lipoprotein lipase (F62336); PLE=pig liver esterase (F46058); TBE=*Thermoanaerobium brockii* esterase (F46061); BSE=*Bacillus* sp. esterase (F46062); SCE=*Saccharomyces cerevisiae* esterase (F46071).

Example 2

Detection of Phytase Activity

1) First implementation: based on the temperature.
   i) 10 mmol of aqueous phytate, pH 5.0, phytase (0.1 mg.ml$^{-1}$), 60 minutes at the indicated temperature;
   ii) 1 mmol of $NaIO_4$, 30 minutes, 26° C.;
   iii) Adjust the pH to 9.0 with 0.1N NaOH, then add 1.5 mmol of nitrophenolamino alcohol, 2 mg.ml$^{-1}$ of BSA, 60 minutes.

Figure 8:
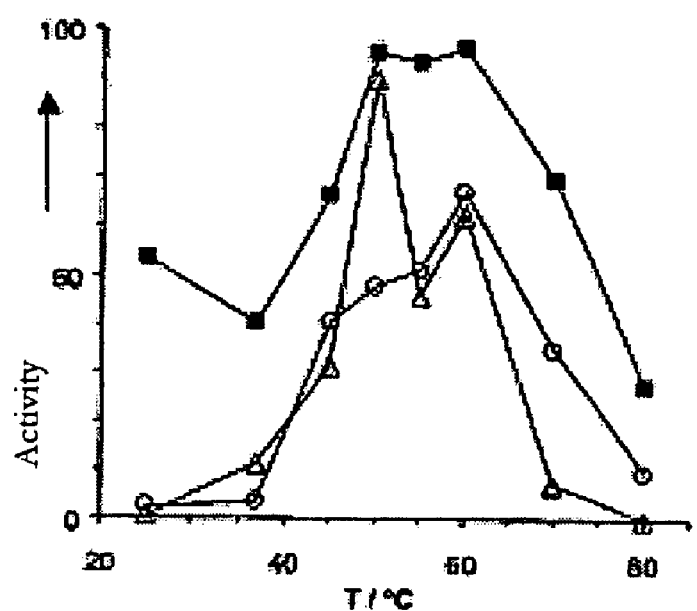
FIGS. 8 and 9 show the results of detecting phytase respectively:
  At different temperatures according to the method of the invention by using nirophenolamino alcohol as a developer.
  At different pH levels by using adrenaline as a developer.

FIG. 8 shows the results of detecting phytase at different temperatures; (■) Natuphos phytase (+1 mmol of CaCl2), (Δ) Novo phytase (+1 mmol of CaCl2), (○) *Apergillus ficuum* phytase (1 mmol of CaCl2+100 nmol of CaCl2). No activity is observed without an enzyme.

2) Second implementation: based on pH.
   i) 10 mmol of aqueous phytate, phytase (0.1 mg.ml$^{-1}$), 55° C., 60 minutes at the indicated pH;
   ii) 1 mmol of $NaIO_4$, 30 minutes, 26° C.;
   iii) Addition of 1.5 mmol of adrenaline, 5 minutes.

Figure 9:
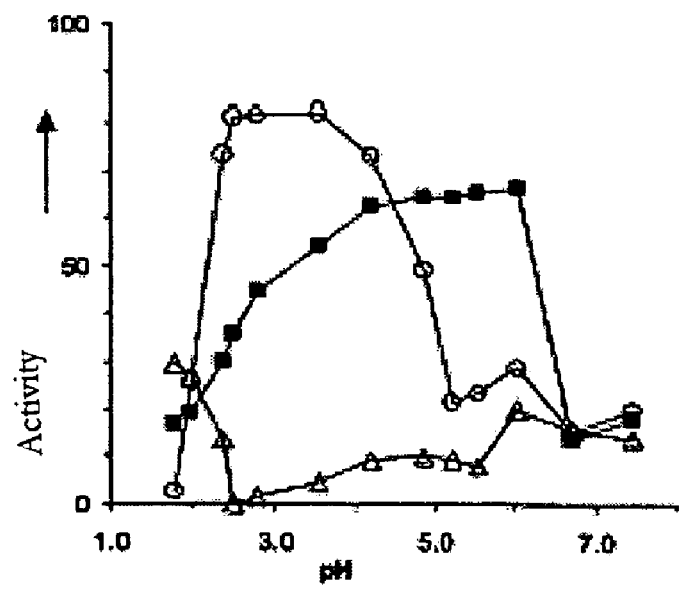

FIG. 9 shows the results are illustrated in the detection of phytase at different pH levels: (■) Natuphos phytase (+1 mmol of CaCl2), (Δ) Novo phytase (+1 mmol of CaCl2), (○) *Aspergillus ficuum* phytase (1 mmol of CaCl2+100 nmol of CaCl2).

Example 3

Detection of Epoxide Hydrolase (EH) Activities

The detection reactions are carried out with the aid of a grid of epoxide substrates 6a–z placed according to FIG. 5.
First Implementation.
   i) 10 mmol of epoxide in 20 mmol of aqueous phosphate, pH 7.2, with the enzyme
   ii) Addition of 1 mmol of $NaIO_4$, 30 minutes, 26° C.; addition of 1.5 mmol of nitrophenolamino alcohol, 2 mg.ml$^{-1}$ of BSA, 60 minutes, 26° C.
   iii) No activity is detected without an enzyme or in the presence of BSA (2 mg/ml).

Figure 10:
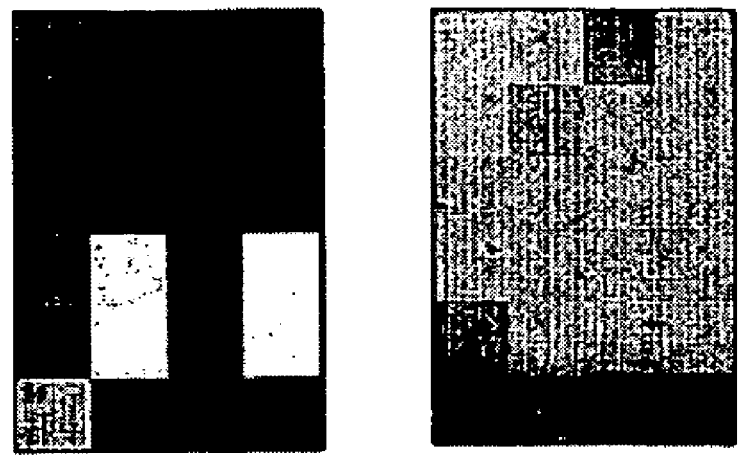
FIGS. 10 and 11 show the results of detecting hydrolase epoxide activities according to the method of the invention respectively by using nitrophenolamino alcohol and adrenaline as developers.

The different results of detection of epoxide hydrolase activities are illustrated in FIG. 10.
2) Second Implementation.
   i) 10 mmol of epoxide in 20 mmol of aqueous phosphate, pH 7.2. with the enzyme and 1 mmol of $NaIO_4$, 30 minutes, 26° C., with 0.05 mg/ml of *aspergillus Niger* EH, or 37° C. with 0.1 mg/ml of *Rhodoturula glutinis* EH.
   ii) Addition of 1.5 mmol of adrenaline, 5 minutes, 26° C.

Figure 11:
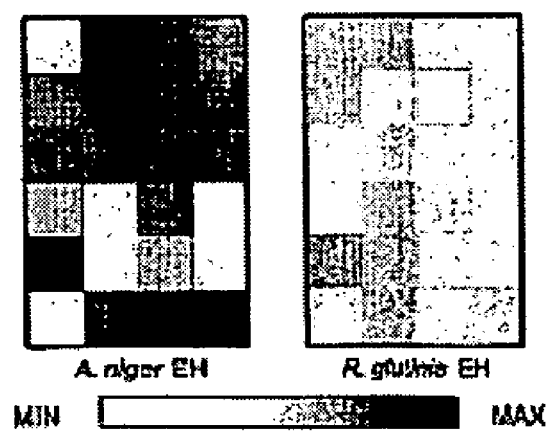
Figure 12:
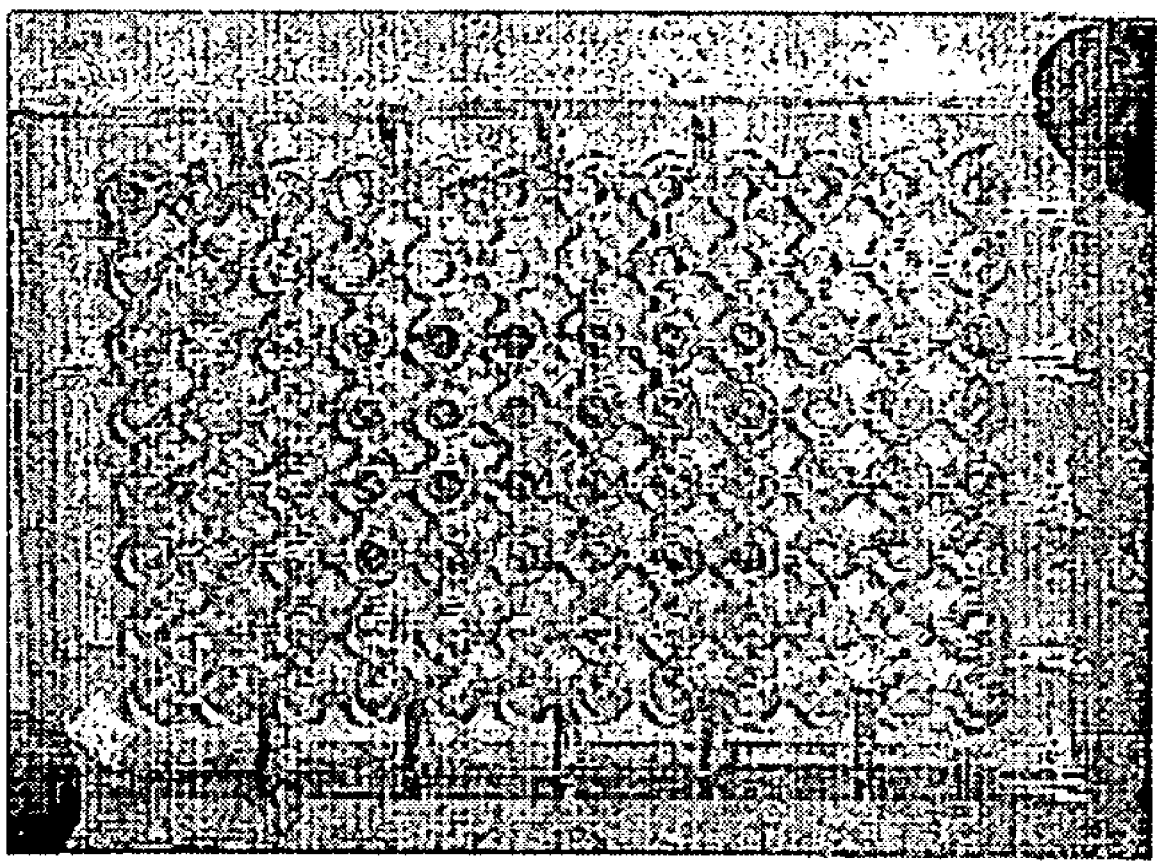
FIG. 12 provides an example on the detection plate for the *Aspergillus Niger* epoxide hydrolase.

FIGS. 10 and 11 show the results of detection of epoxide hydrolase activities:
   FIG. 10: Grid of epoxide substrates 6a–z placed according to FIG. 5. To the left: *Aspergillus niger* EH (50 μg.ml$^{-1}$), 60 minutes, 26° C.; to the right: *Rhodoturula glutinis* EH (0.5 mg.ml$^{-1}$), 37° C., 120 minutes.
   FIG. 11: Grid of epoxide substrates 6a–z placed according to FIG. 5. To the left: *Aspergillus niger* EH (50 μg.ml$^{-1}$), 30 minutes, 26° C.; to the right: *Rhodoturula glutinis* EH (0.1 mg.ml$^{-1}$), 37° C., 30 minutes.
   FIG. 12 gives an example on a detection plate of the epoxide hydrolase (EH) of *Asperillus Niger*, carried out by direct development with adrenaline. Conditions: pH 7.2, 25 microg/ml of enzyme, 10 mmol of substrates, 1 mmol of $NaIO_4$, 30 minutes, then addition of 1.5 mmol of adrenaline, instantaneous reaction (<30 seconds). The colored wells are those where the periodate has not been consumed by the diol that is formed by hydrolyses of epoxides, there where no reaction has taken place (monitoring from top left).

What is claimed is:
1. A method for detecting catalytic activity of a sample comprising:
   (i) contacting the sample with a substrate (S);
   (ii) adding a reagent (X), said reagent being reactive with a chemical group of substrate (S) or with a chemical group of a product (P), wherein product (P) results from catalytic activity between the sample and the substrate (S), wherein reagent (X) does not react simultaneously with the substrate (S) and product (P);

(iii) adding a developer (R), said developer being reactive with reagent (X); and
(iv) detecting a transformation of developer (R), said detecting being insensitive to substrate (S) and product (P).

2. The method of claim 1, wherein the catalytic activity of the sample is chemical or enzymatic.

3. The method of claim 2, wherein the catalytic activity of the sample corresponds to at least one enzyme comprising hydrolases, oxydases, lyases, ligases, transferases, isomerases, or a combination thereof.

4. The method of claim 1, wherein the sample is chemical, biological, microbiological, animal, vegetable, or a combination thereof.

5. The method of claim 1, wherein the chemical group of substrate (S) or product (P) comprises 1,2-diol, 1,2-amino alcohol, 1,2-diamine, alpha-hydroxyketone, alpha-aminoketone, thiol, thioether, or hydroquinone (=1,4-dihydroxybenzene) groups.

6. The method of claim 1, wherein substrate (S) and/or product (P) correspond to a compound:

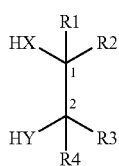
(I)

wherein the C1-C2 bond is sensitive to a cleavage by a chemical oxidation reaction and wherein (a) R1 to R4 comprise a hydrogen atom, or a functional group that may or may not be substituted, and (b) X and/or Y comprise an oxygen atom, a sulfur atom, an amine of formula —$NR_8R_9$ wherein $R_8$ comprises a hydrogen atom, an alkyl group, or an aryl group and $R_9$ does not comprise a hydrogen atom.

7. The method of claim 6, wherein at least one of R1 to R4 correspond to a formula:

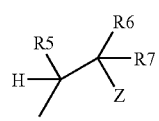
(IV)

wherein R5, R6 and R7 comprise a hydrogen atom, or a functional group that may or may not be substituted, and wherein Z is precursor of a detectable product ZH;
wherein ZH comprises an aromatic alcohol, a heteroaromatic amine, a halogen atom or a phosphoric ester.

8. The method of claim 1, wherein reagent (X) is a fluorescent hydrazine F1-$NHNH_2$, and developer (R) is an aldehyde or ketone F2-CHO, such that a FRET phenomenon between F1 and F2 can be observed.

9. A method for detecting catalytic activity of a sample comprising:
(i) contacting the sample with a substrate (S);
(ii) after an incubation period between substrate (S) and the sample, adding a reagent (X) that is reactive with either the substrate (S) that is not consumed by the catalytic activity of the sample or a product (P) formed by catalytic activity between the sample and the substrate (S);
(iii) adding a developer (R), said developer being reactive with reagent (X); and
(iv) detecting a transformation of developer (R).

10. The method of claim 9, wherein the developer (R) comprises adrenaline, noradrenaline or octopamine.

11. The method of claim 9, wherein developer (R) is a precursor of an inhibitor of a catalyst and wherein, in the presence of the reagent (X), the precursor of the inhibitor is transformed into an inhibitor of a catalyst of a detectable reaction, whereby said catalyst is different from the catalytic activity of the sample.

12. A method for detecting catalytic activity of a sample comprising:
(i) contacting the sample with a substrate (S), wherein, after an incubation period, at least a portion of the substrate (S) catalytically reacts with the sample to form a product (P);
(ii) after the incubation period between substrate (S) and the sample, adding a reagent (X) comprising a chemical oxidizing agent;
(iii) adding a developer (R), said developer being reactive with reagent (X); and
(iv) detecting a transformation of developer (R);
wherein the product (P) and developer (R) have chemical groups comprising 1,2-diol, 1,2-amino alcohol, 1,2-diamine, alpha-hydroxyketone, alpha-aminoketone, thiol, thioether, catecholamine, or hydroquinone.

13. The method of claim 12, wherein the chemical oxidizing agent comprises: $H_5IO_6$, $RuO_2$, $OsO_4$, $(CH_3CH_2CH_2)_4 N(RuO_4)$, $NaClO_4$, $NaIO_4$, $Na_3H_2IO_6$, $NaMnO_4$, $K_2OsO_4$, $KIO_4$, $KMnO_4$, $KRuO_4$, $K_2RuO_4$, LiOCl, lead acetate, tetrapropyl ammonium periodate, chromic acid or salts of the latter, $NaBiO_3$, $Ph_3BiCO_3$, $Ca(OCl)_2$, reagents Ce(IV), Cr(VI), salts of Co(II),IOAc, I(OAc)$_3$, N-iodosuccinimide, VO(acac), $Pb(OAc)_4$, $MnO_2$, $H_2O_2$ or mixture of reagents [$H_2O_2$, $Na_2WO_4$, $H_3PO_4$].

14. The method of claim 12, wherein the developer (R) comprises one of the following formulas:

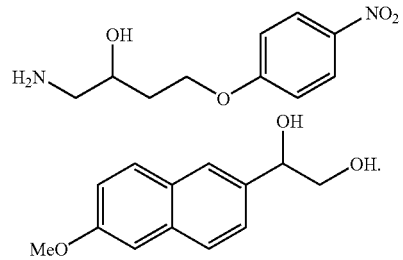

15. The method of claim 1, wherein the animal is a human.

16. The method of claim 5, wherein the 1,2-diol is a catechol.

17. The method of claim 12, wherein the 1,2-diol is a catechol.

18. The method of claim 6, wherein the functional group that may or may not be substituted is an alkyl group that may or may not be substituted.

19. The method of claim 7, wherein the functional group that may or may not be substituted is an alkyl group that may or may not be substituted.

20. The method of claim 7, wherein the aromatic alcohol is a heteroaromatic alcohol.

* * * * *